United States Patent
Dishongh et al.

(10) Patent No.: US 7,602,275 B2
(45) Date of Patent: Oct. 13, 2009

(54) CONTEXTUAL MEDICATION PROMPTING PILLBOX

(75) Inventors: Terrance Dishongh, Portland, OR (US); Kevin Rhodes, Beaverton, OR (US); Jay Lundell, Portland, OR (US); Kofi Cobbinah, Houston, TX (US); Bradford Needham, North Plains, OR (US)

(73) Assignee: Intel Corporation, Santa Clara, CA (US)

( * ) Notice: Subject to any disclaimer, the term of this patent is extended or adjusted under 35 U.S.C. 154(b) by 322 days.

(21) Appl. No.: 11/644,017

(22) Filed: Dec. 22, 2006

(65) Prior Publication Data

US 2008/0149659 A1  Jun. 26, 2008

(51) Int. Cl.
*G08B 1/00* (2006.01)
(52) U.S. Cl. .............................. 340/309.16; 340/573.1; 340/539.12
(58) Field of Classification Search .............. 340/539.1, 340/573.1, 309.16, 539.12, 539.13, 539.15
See application file for complete search history.

(56) References Cited

U.S. PATENT DOCUMENTS

| | | | | |
|---|---|---|---|---|
| 5,954,225 A | * | 9/1999 | Powe | 221/2 |
| 6,002,994 A | * | 12/1999 | Lane et al. | 702/188 |
| 6,145,697 A | * | 11/2000 | Gudish | 221/3 |
| 6,313,733 B1 | * | 11/2001 | Kyte | 340/7.22 |
| 6,771,174 B2 | * | 8/2004 | Broas | 340/573.1 |
| 7,158,011 B2 | * | 1/2007 | Brue | 340/309.16 |
| 2007/0257051 A1 | * | 11/2007 | Abdulhay et al. | 221/2 |
| 2008/0119958 A1 | * | 5/2008 | Bear et al. | 700/244 |

* cited by examiner

*Primary Examiner*—Jeffery Hofsass
(74) *Attorney, Agent, or Firm*—Pillsbury Winthrop Shaw Pittman LLP (57) ABSTRACT

A medication box may include a processor, a plurality of compartments configured to store medication and a transceiver capable of communication with a patient via a user or patient device which is within communication range of the medication box. A server which may be configured to communicate information stored by the processor to a third-party device via wired or wireless communication methods. An estimated distance between the medication box and an RF patient device can be determined by a received signal strength indicator measured by the medication box or by the RF patient device.

30 Claims, 7 Drawing Sheets

FIG.1

Actuation distance of lmed based on the reed switch

FIG. 2a

Tic Tac Measurement

CONTEXTUAL MEDICATION PROMPTING PILLBOX

FIELD OF INVENTION

The embodiments of the invention relate to a contextual medication reminder, and more particularly to a device that is aware of the activities of the person in a medication regime and drives a prompt to the person through various means, based on the activity taking place.

BACKGROUND

There currently exist a number of medications reminding systems. These systems are time-based and do not consider the context required to drive a prompt or reminder.

Typical products on the market for medication adherence fall along two paths. The first is a product that acts like a timer or an alarm clock. These devices issue alarms when the time arrives for a person to be reminded to take their medication. Although these devices are highly accurate in measuring time and delivering an alarm, the user is often not co-located with the medication at the time of alarm. At the other extreme, alarms loud enough to be heard throughout the house became such a nuisance that they are often ignored for prompting too often. Other typical devices are storage and dispensing types of devices. These are common in many households and take the form of a box with compartments in multiples of seven for the days of the week. Medication is stored in these devices and the device is often located near the activity center associated with the time of day the medication should be taken. However, these systems fail when the user's routine is disturbed.

DETAILED DESCRIPTION

A medication box according to an embodiment of the invention includes a processor, a plurality of compartments configured to store medication and a transceiver capable of communication with a patient via a user or patient device which is within communication range of the medication box. The plurality of compartments have compartment doors which may be configured to open and close the plurality of compartments. The plurality of compartment doors may also have switches capable of detecting whether the compartments door are open or closed. The switches may be magnetic reed switches which are capable of detecting an open or closed state of the compartment door depending on whether the compartment door is opened a predetermine distance.

The medication box according to another embodiment of the invention may include an LCD, a speaker, a user input device and a clock. The LCD may be capable of providing information including at least a time of day, a date, and a pill to be taken at a particular time and capable of presenting at least one question to a user or patient. The user input device may include at least one input button which is configured to allow a user to manipulate the LCD and which is also configured to allow a user or patient to respond to respond to requests for information. The speaker may be configured to present questions to a user or patient on a daily basis or at preset times. The user input device may be configured to allow the user to answer the questions presented by the speaker and the processor may be configured to store data relating to the information input by the user input device.

The medication may also include a server which is configured to communicate information stored by the processor to a third-party device via wired or wireless communication methods. The server may be configured to facilitate communication of information from the medication box over the Internet to a third-party device. The transceiver may enable the medication box to be configured remotely and can be configured to measure signal strength and link communications quality of a radio signal which enables the medication box to determine information about a relative location of the medication box and the patient device that is an RF patient device which is capable of wirelessly communicating with the medication box.

The medication box may also be capable of prompting a patient to take a particular medication if the transceiver determines that the patient is within sufficiently close range of the medication box.

According to an embodiment of the invention, an estimated distance between the medication box and the RF patient device can be determined by a received signal strength indicator measured by the medication box or by the RF patient device.

According to another embodiment of the invention, a medication reminder system may include a medication box having a processor, a plurality of compartments configured to store medication and a transceiver; an RF patient device capable of wireless communication with the medication box, wherein the medication box is configured to determine information about the location of the medication box relative to the RF patient device and to prompt a user or patient to take medication at a predetermined time. The medication box of the medication reminder system may also include an LCD, a speaker, a user input device and a clock. The medication reminder system may also in clued a server which is configured to communicate information stored by the processor to a third-party device via wired or wireless communication methods. The server may be configured to facilitate communication of information from the medication box over the Internet to a third-party device.

A medication reminding system according to an embodiment of the invention may include a medication box that contains an embedded processor, an LCD, a user input device, such as buttons located on the medication box, doors on the medication box that have respective door switches, a real time clock (RTC), and a radio transceiver. The enclosure for the device according to an embodiment of the invention is seen in FIG. 1.

According to this invention, a processor may include a microprocessor, which is a programmable digital electronic component that incorporates the functions of a central processing unit (CPU) on a single semi-conducting integrated circuit (IC). The processor may interpret computer program instructions and processes data.

Figure 1:
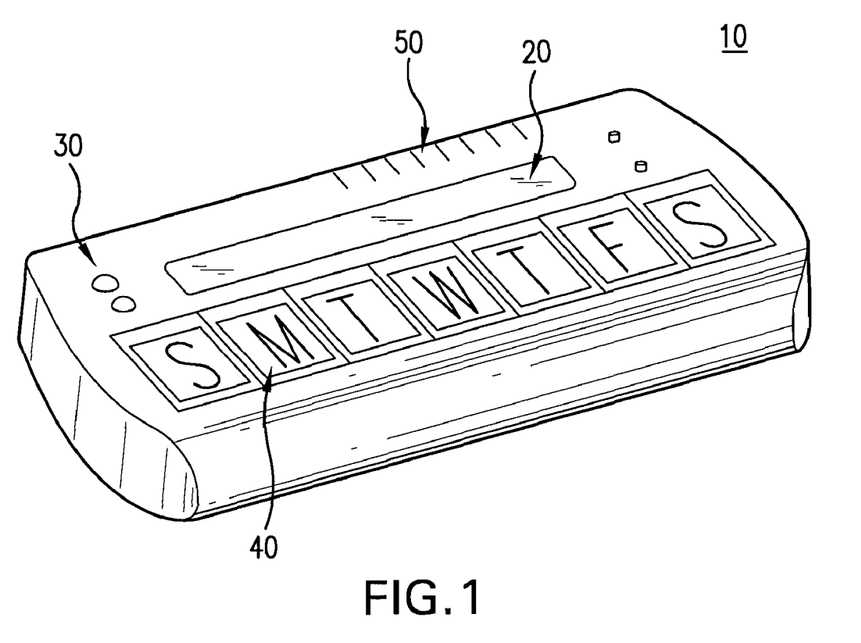
FIG. 1 shows a medication box according to an aspect of the invention.

As shown in FIG. 1, the medication box 10 can include a plurality of compartments 40 which hold various pills. These compartments can be labeled to correspond to days of the week. An LCD display 20 can be provided to display information such as the time, the date, what pill should be taken at a particular time, etc. A user input device 30, which may include one or more buttons, may be used by a user to manipulate the display or respond to requests for information. A speaker 50 may be included to alert the user that it is time to take a particular medicine. Other types of reminders or alarms can be transmitted to the user through the speaker 50. A reminder message may also be displayed as a text message on the LCD display 20. The LCD display 20 or speaker 50 may also present a set of questions to the user on a daily basis or at preset times. The questions can be tailored to enquire about potential side effects of drugs, the quality of sleep, the health status of patient, etc. and physicians can use the answers to these questions to measure the well-being of the patient without the patient necessarily visiting their doctor. The user can use the user input device 30 to answer any questions asked. There may also be a device embedded in the medication box which can record verbal answers to the questions posed to the user/patient. According to various aspects of the invention, an Electrically Erasable Programmable Read-Only Memory (hereinafter, "EEPROM") may be included in the device as a non-volatile storage chip to store information in the device.

EEPROMs typically come in a range of capacities from a few bytes to over 128 kilobytes and are often used to store configuration parameters. In some systems, EEPROMs have been used in lieu of CMOS nonvolatile BIOS memory. For example, in personal computers EEPROMs are often used to store the BIOS code and related system settings. EEPROMs may be erased electrically in-circuit, and may be used for 100,000 erase-write cycles or more. EEPROMs typically retain data when power is not supplied. EEPROM chips may use serial interfaces to connect to other devices.

Additionally, the medication box may contain a wired or wireless communication device (not shown), in order to load configuration settings from a server, or to send patient responses and door-opening information to a server. Such wired or wireless communication of data and/or voice may include, but are not limited to, the following: 802.11 wireless network protocol; Bluetooth protocol; 802.15.4 protocol; wired network protocol; telephone line; infrared data transfer; acoustic coupler; RS-232 serial transfer; manual transfer via memory card, Near Field Communication or RFID. The preferred embodiment contains a Bluetooth radio which connects to an in-home server which is, in turn, connected to the Internet.

The heart of an RFID system lies in an information carrying tag called an RFID tag, which functions in response to a coded RF signal received from a base station or an RFID reader. Typically, an RFID tag reflects an incident RF carrier back to the base station or reader, and information is transferred as the reflected signal is modulated by the RFID tag according to its programmed information protocol.

Generally an RFID tag has a semiconductor chip having RF circuits, various logic circuitry, and a memory, as well as an antenna, a collection of discrete components, such as capacitors and diodes, a substrate for mounting the components, interconnections between components, and a physical enclosure. Two types of RFID tags are generally used, active tags, which utilize batteries, and passive tags, which are either inductively powered or powered by RF signals used to interrogate the tags; passive tags do not use a battery.

Generally, passive RF tags contain of two basic parts: an analog circuit which detects and decodes the RF signal and provides power to a digital portion of the tag using RF field strength from the reader, and a digital circuit which implements multiple items of tag identification protocol.

A radio frequency (RF) identification system generally consists of an RF reader and a plurality of RF tags. In a typical configuration, the reader utilizes a processor which issues commands to an RF transmitter and receives commands from the RF receiver. The commands serve to identify tags present in the RF field.

In some implementations, commands exist to gather information from the tags. In more advanced systems, commands exist which output information to the tags. This output information may be held temporarily on the tag, it may remain until written over, or it may remain permanently on the tag.

The RF transmitter of the reader generally encodes commands from the processor, modulates the commands from a base band to the radio frequency, amplifies the commands, and then passes the commands to the RF antenna. The RF receiver receives the signal at an antenna, demodulates the signal from the RF frequency to the base band, decodes the signal, and passes it back to the processor for processing. The reader's antenna is usually capable of transferring RF signals to and from a plurality of tags within the RF signal range.

Radio Frequency Identification is a type of automatic identification method, which utilizes storing and remotely retrieving data using devices called RFID tags or transponders. Chip-based RFID tags generally contain silicon chips and antennas. Passive tags generally do not use an internal power source, whereas active tags generally do incorporate a power source. RFID cards, also known as "proximity" or "proxy" cards, come in three general varieties: passive, semi-passive (also known as semi-active) and active.

Passive RFID tags generally have no internal power supply. A minute electrical current induced in an antenna by incoming radio frequency signals generally provide enough power for an integrated circuit (hereinafter, "IC"), e.g. a CMOS based IC, in the tag to power up and transmit a response. Most passive tags provide a signal by backscattering the carrier signal received from an RFID reader. In order to utilize backscattering, the antenna of a passive RFIC tag is generally configured to collect power from the incoming signal and to transmit an outbound backscatter signal. The response of a passive RFID tag is not limited to an ID number (e.g. GUID); many RFID tags contain nonvolatile memory devices, such as EEPROMs, for storing data. Common passive RFID tags may commonly be read at distances ranging from about 10 cm to a several meters, depending on the chosen radio frequency and antenna design/size.

Unlike passive RFID tags, active RFID tags generally have internal power sources which are used to power incorporated ICs that generate an outgoing signal. Active tags may be more reliable (e.g. fewer errors) than passive tags because the active tags may conduct a session with a reader where error correction and/or signal verification may be utilized. Active tags may also transmit at higher power levels than passive tags, allowing them to be more effective in "RF challenged" environments such as water or metal, and over greater distances. Many active RFID tags have practical ranges of hundreds of meters, and a battery life of up to 10 years.

In a typical RFID system, an RFID reader may be contain an antenna packaged with a transceiver and decoder. The RFID reader may emit a signal activating the RFID tag so it can read data from and write data to the RFID tag. When an RFID tag passes through the electromagnetic zone, it detects the reader's activation signal and is activated. The reader may then decode the data encoded in the tag's IC and may either store the data of pass the data to a processor.

Depending on the type of system utilizing the RFID reader, application software on a host computer may process the data in a myriad of different ways, e.g. the data may be filtered to reduce redundant readings of the same tag and to form a smaller and more useful data set.

Near Field Communication (hereinafter, "NFC") is a new, short-range wireless connectivity technology that evolved from a combination of existing contact free identification and interconnection technologies. Products with built-in NFC may simplify the way consumer devices interact with one another, helping speed connections, receive and share information and even making fast and secure payments.

Commonly operating at 13.56 MHz and transferring data at up to 424 Kbits/second, NFC provides intuitive, simple, and safe communication between electronic devices. NFC is both a "read" and "write" technology. Communication between two NFC-compatible devices may occur when the devices are brought within approximately four centimeters of one another: a simple wave or touch may establish an NFC connection which is then compatible with other known wireless technologies such as Bluetooth or Wi-Fi. Because the transmission range may be relatively short, NFC-enabled transactions are inherently secure. Also, physical proximity of the device to the reader gives users the reassurance of being in control of the process.

NFC may be used with a variety of devices, from mobile phones that enable payment or transfer information to digital cameras that send their photos to a TV set with just a touch.

Bluetooth is an industrial specification for wireless personal area networks (PANs). Bluetooth provides a way to connect and exchange information between devices such as mobile phones, laptops, PCs, printers, digital cameras and video game consoles via a secure, globally unlicensed short-range radio frequency. Bluetooth is a radio standard and communications protocol primarily designed for low power consumption, with a short range (power class dependent: 1 meter, 10 meters, 100 meters) based around low-cost transceiver microchips in each device. Bluetooth lets these devices communicate with each other when they are in range. The devices use a radio communications system, so they do not have to be in line of sight of each other, and can even be in other rooms, so long as the received transmission is powerful enough.

According to various embodiments of the invention, the device may utilize a transceiver to transmit and/or receive information. Typically, a transceiver is a device that has a transmitter and a receiver which may be combined. Technically, transceivers generally combine a significant amount of the transmitter and receiver handling circuitry. Similar devices may include transponders, transverters, and repeaters. Generally, a transceiver combines both transmission and reception capabilities within a single housing. The term transceiver, as used herein may refer to a device, such as an RFID tag or an NFC device. These devices may receive data over a hardwired connection or a radio frequency connection, as well as through various other types of connection. The devices may transmit information over similar of different connections.

Each compartment 40 of the medication box 10 may contain a magnetic reed switch where each compartment door contains a corresponding magnet. Additionally, each compartment door preferably has a tactile, "snap shut" latch. The magnet of the reed switch is chosen such that when the door is opened enough to insert a finger or pour out a pill, the magnetic reed switch reads "open," yet when the door is only resting slightly open (the latch has not snapped closed) the magnetic reed switch reads the door as being "closed." This arrangement allows the switch to distinguish the situation in which the compartment door is left slightly ajar, but not enough to remove a pill, from the situation in which the compartment door is open sufficiently to remove a pill.

Figure 2A:
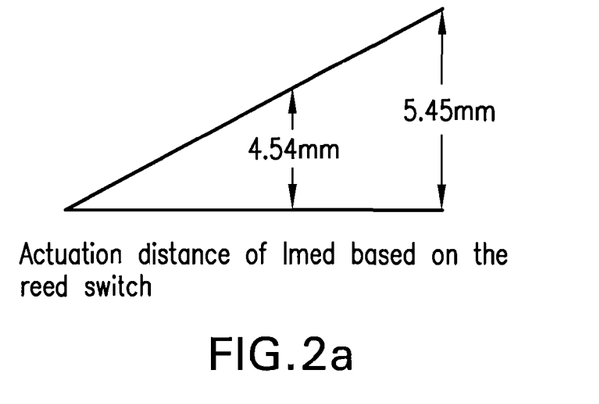
FIG. 2a shows a typical actuation distance of the compartment door based on use of a magnetic reed switch.
Figure 2B:
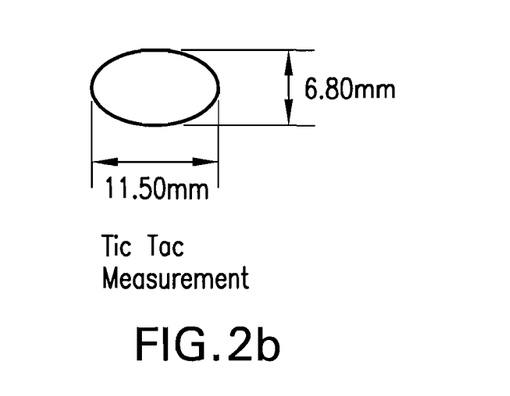
FIG. 2b shows a measurement of a typical pill size.

The reed switch, with the help of gravity, actuates even if the compartment door is not closed completely (not snapped closed). When a user lifts the compartment door enough to insert their finger to take the medication, the reed switch shows that the door is open. An experiment was done with a ¼" by ¹⁄₁₆" ferrite magnet. In this experiment, it was found that the reed switch actuated (it read "closed") when the magnet was within a distance of 0-5.45 mm (millimeters) and it read "open" when the compartment door was within anything from 6 mm and above the snapped closed position. FIGS. 2a and 2b illustrate a typical actuation distance of the compartment door based on use of a magnetic reed switch.

Figure 3:
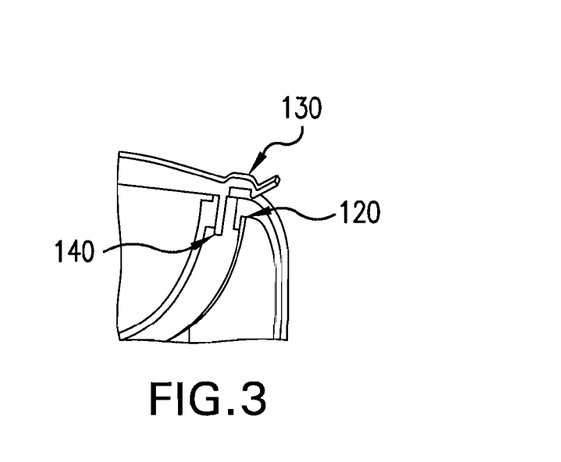
FIG. 3 shows an example of a reed switch according to an embodiment of the invention.

As shown in FIG. 2a, since the average person's pinky finger ranges from about 4 mm-12 mm, and it is assumed that that the minimum tablet for medication is the size of a common Tic Tac (see FIG. 2b), the reed switch will indicate when the compartment door of the medication box has been opened or closed, enabling the device to infer that medication has been taken. Each compartment door may contain an LED (not shown), which can be used to prompt the user as to which door to open—that is, which pill to take. An example of a reed switch is shown in FIG. 3, where the reed switch 120 may include a magnet holder 130 and a notch latch 140 to ensure positive feedback.

In an alternative embodiment, the compartment door switch may be combined with the compartment light in the following way: the circuit board inside the medication box contains one lighted switch per compartment; a light pipe (a translucent cylinder in this case) rests on the lighted switch while the other end of the light pipe presses up against the compartment door. When the switch is light, the light travels up the light pipe to illuminate the corresponding compartment door. Also, the light pipe transfers the mechanical pressure from the switch to the compartment door, acting as a spring for the door. In this way, when a compartment door is closed, the pressure on the corresponding light pipe transfers pressure to the appropriate switch and closes it.

Each compartment is illuminated separately such that if a medication regime is being followed, the LED can be used to prompt for the right day at the right time. These LED's have a separate application in that they may be used to prompt the user to close an open lid completely to ensure that future pill-taking can be detected.

The medication reminding system can be both wall powered and battery powered. Activities performed on the system when it is in battery mode are stored in the system's database. When the medication device is wall powered again, the stored information is transferred to a computer, and later can be viewed by a second or third party.

Figure 4:
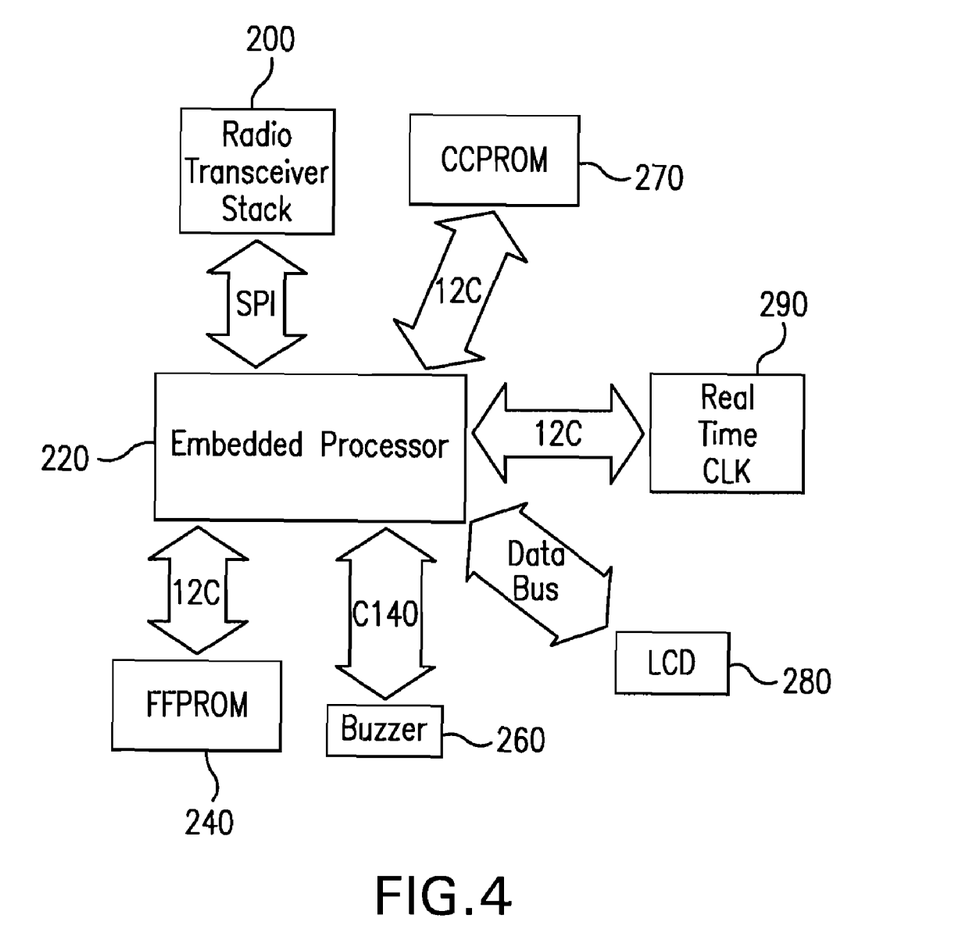
FIG. 4 shows the electronic components inside the medication box according to an embodiment of the invention.

FIG. 4 depicts the electronic components inside the medication box. The radio transceiver 200 allows the medication box to be configured remotely and allows transfer of pill-taking data, as described earlier. Additionally, the radio transceiver 200 can measure the signal strength and link communications quality of the radio signal (RSSI and LQ), enabling the pillbox to determine information, described below, about the relative location of the pillbox, the computer it communicates with via RF, and/or an RF device the patient wears. EEPROM 270 provides storage for pill-taking information and patient responses. Real-time clock 290 enables the time-stamping of data so that the system can mark each piece of data with the time the corresponding event (such as taking a pill) happened. The LCD 280 is described above. Buzzer 260 is a piezoelectric buzzer, the preferred embodiment of the speaker described above. Embedded processor 220 controls the behavior of the medication box, including its communication of data, location, and configuration information.

The medication reminding system is also capable of prompting a patient to take medication when in close range of the system's radio signals, or a predetermined distance, if the patient has not already taken the appropriate pill for this time period based on the door open and closed signal timing. The system may use Bluetooth radio capabilities to track the proximity of the user if the user is wearing a Bluetooth enabled device such as a watch, a pacemaker, a compartment phone, a personal digital assistant (PDA), etc. In one embodiment, the fact that the user is within range (i.e., a predetermine distance) of the system is determined simply by the detection of a radio signal of the pillbox by the user's radio device, or by the detection of a radio signal of the user's radio device by the pillbox. In another embodiment, the rough distance between the pillbox and the user's radio device is determined by the RSSI (Received Signal Strength Indicator) measured by the pillbox or by the patient's radio device.

In still another embodiment, the pillbox is capable of determining its location relative to the computer it communicates with, by a method describe in detail below. In yet another embodiment, the pillbox is capable of determining the location of the patient's radio device by the same method.

According to various embodiments of the invention, the device may utilize a system based on Received Signal Strength Indicator (hereinafter, "RSSI") technology to determine a location of the device. RSSI is a known term in the field of radio engineering, and is a common feature designed in most radio transceivers systems. In a common dielectric medium, the emission of the radio waves from transmitters the RSSI is known to decay as a power function as the distance between the transmitter and receiver are increased. In the device and method describe wherein the medium is known to be a discontinuous dielectric thereby reducing the decay of the RSSI to a near liner function of the distance between the receiver and transmitter increases.

Existing indoor location tracking techniques rely on the RSSI (Received Signal Strength Indicator) of two or more receivers. This is an issue in Bluetooth-based location tracking because the device that is the Bluetooth master can connect to at most eight slaves in a pico-net, dictating that each stationary radio (in one embodiment, the pillbox) that wishes to contribute an RSSI value is a slave to a mobile master (in one embodiment, the patient's radio device). In that case, other devices can not communicate with the master to save data. According to an embodiment of the invention, the mobile device (the patient's radio device) is used as a slave in the network rather than a master. While this solves the problems of having a mobile master, it restricts the number of masters that can speak to the mobile device to one, which would normally produce too few RSSI signals to locate the mobile device. In contrast, according to an embodiment of the invention, a single master's RSSI and radio Link Quality measures are used to locate the mobile device within the house.

Figure 5:
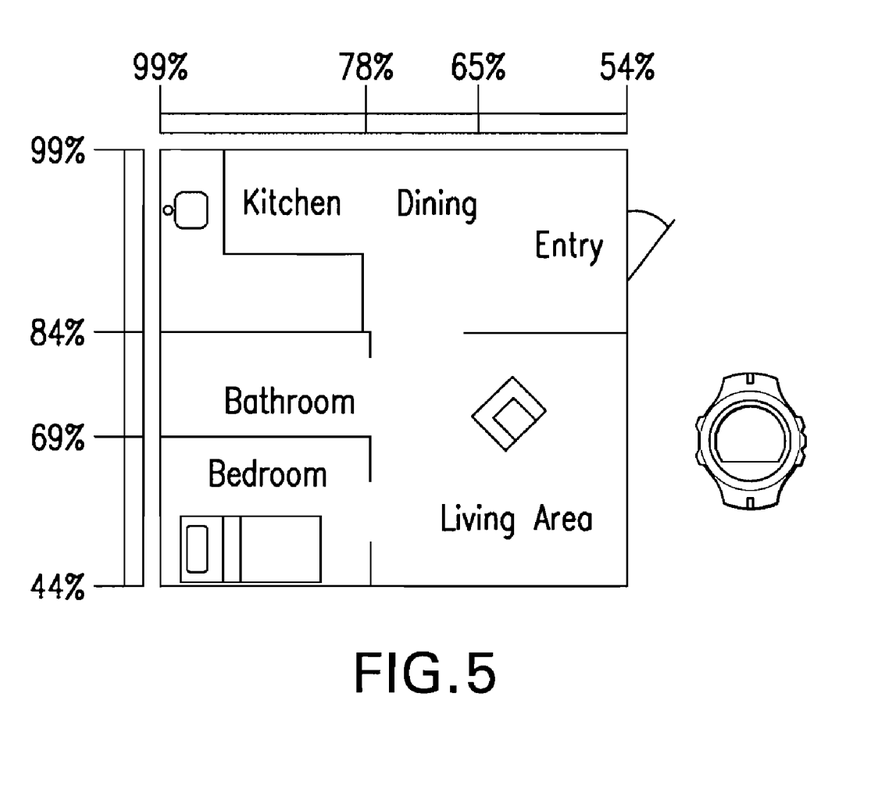
FIG. 5 shows an apartment floor plan with an idealized map of RSSI values based on the location of the patient's radio device within the apartment according to an embodiment of the invention.

FIG. 5 shows an apartment floor plan; a pillbox 10 in the upper-left corner of the apartment, with an idealized map of RSSI values based on the location of the patient's RF device within the apartment. Each dark arc represents a line of equal RSSI, and the scale along the top of the figure shows the RSSI value corresponding to each line. For example, if the patient and their associated radio device (RF patient device 300) is in the living area, the RSSI signal measured by the pillbox in the kitchen would by approximately 60%.

In FIG. 5, the Bluetooth Master (pillbox 10) may infer from its 60% RSSI value that the patient (actually, the patient's radio device) may be in the bedroom, living room or the dinning area—RSSI alone is not sufficient to determine the location of the mobile device within the apartment. In most instances, due to radio signal reflections, absorption, and multi-path interference caused by the walls and furniture in the apartment, the RSSI map will be much more complex. Even in the case of a complex RSSI map of the apartment, areas of equal RSSI (and therefore ambiguous location) exist.

In one embodiment, the pillbox radio uses RSSI and Link Quality to infer the location of the patient's radio device. In a home, there are various points in which a radio signal is bounced, or partially blocked. These locations are unique to a home and position of the devices, and home construction, and furnishings. As such, the LQ (Link Quality; also called BER, the bit error rate), that is to say, the number of collisions of packets in transmission or non-received packets, is somewhat uncorrelated with the radio signal strength. For example, the signal strength may be high but due to multi-path interference the Link Quality (bit error rate) may be low. Similarly, the RSSI may be low enough to eliminate some multi-path reflections, causing the Link Quality to be high.

Figure 6:
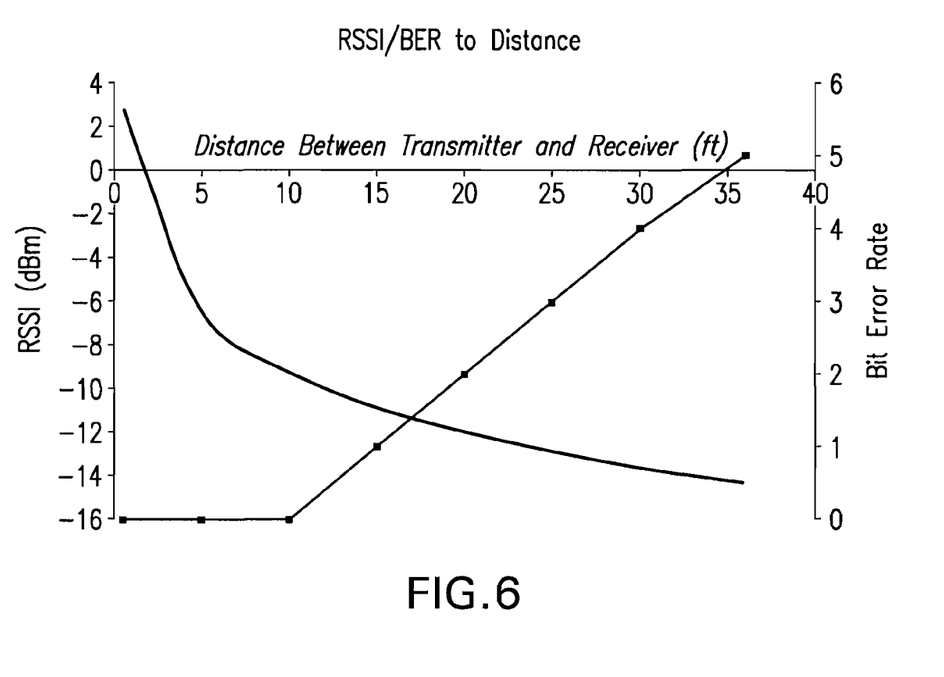
FIG. 6 is a graph that shows how the RSSI decays to the fourth power as distance between the receiver and the medication box increases according to an embodiment of the invention.
Figure 7:
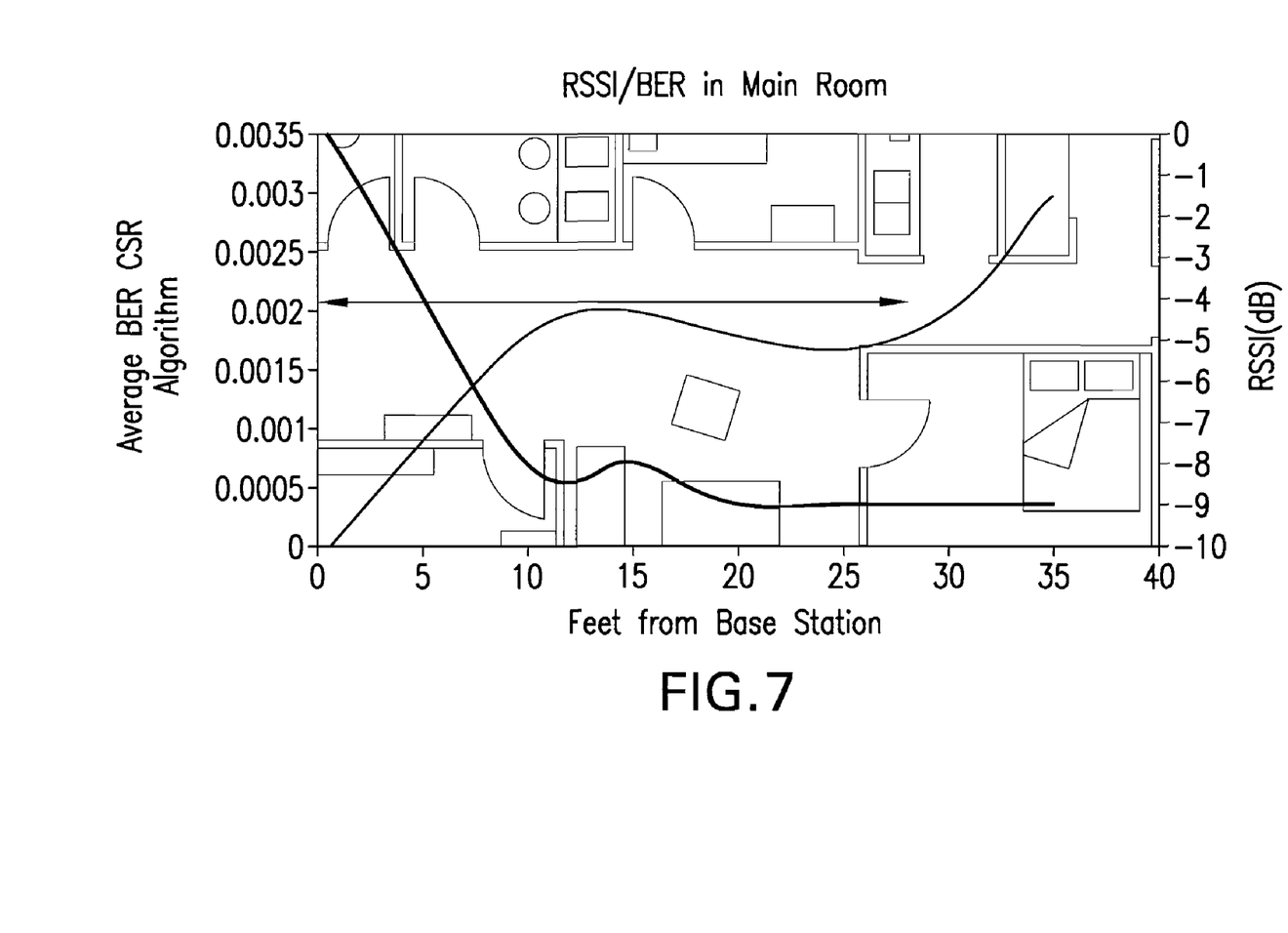
FIG. 7 is a graph that shows the RSSI and BER (LQ) graphs measured in an apartment according to an embodiment of the invention.

In free space or an open field, the RSSI decays to the fourth power as distance between the receiver and the medication box increases. FIG. 6 illustrates this effect. In free space, the RSSI decays to the fourth power whereas the bit error rate increases linearly as the distance increases beyond a minimum distance. At distances less than a minimum distance specific to the radios and power involved, RSSI is at a constant, high value and BER is at a constant low value; at distances larger than a maximum distance, again determined by the radios and power, RSSI is zero and BER is 100%. In contrast to their free space behavior, RSSI and BER in a home also vary based on the construction and contents of the home. FIG. 7 shows the same RSSI and BER (inverse of LQ) graphs measured in an apartment. In FIG. 7, the Bit Error Rate (BER) is less tied to the distance and more tied to multi-path issues caused by the signal being reflected and/or absorbed by walls and furniture in the apartment. Reflected signals can reinforce each other, causing lower BER (better reception) than expected in free space, or can partially or completely cancel each other, causing a higher BER (worse reception) than expected in free space.

Notice that the RSSI in FIG. 7 (the line that falls from left-to-right) falls as expected and the combination of BER (Bit Error Rate) and RSSI provides the unique signature of the two walls, at 12 feet and 26 feet from the radio base station. Thus, the combination of RSSI and BER in the home can give a unique signature of the position of a signal pair transmitter and receiver.

In the preferred embodiment, the RSSI and LQ (BER) values are read at the end of each periodic burst of communication between the pillbox and the patient's radio device, because in Bluetooth protocol those values can be read only after successful communication between the devices.

The {RSSI, LQ} pair measured at the end of a burst of communication is used to look up the corresponding physical location in a previously acquired table of the {RSSI, LQ} values for each location in the house. To create this table, the patient (or just their radio device) is moved to each location within the house, for example in a grid of 2 ft by 2 ft, and the mean and standard deviation RSSI and LQ values for each physical location are recorded. According to one embodiment, the resulting table is an array where each row in the array contains {mean RSSI, standard-deviation RSSI, mean LQ, standard-deviation LQ, associated physical location}, where physical location consists of the distance, in feet in two dimensions of a measured grid location on the floor of the house. In that embodiment, to find the location of the mobile radio relative to the medication box within the house, the current RSSI and LQ values are measured, then a lookup algorithm finds the array row whose {RSSI, LQ} value is nearest to the measured {RSSI, LQ} value. Once the nearest row is found, the algorithm returns the physical location from that row, such as "15 feet East of the NorthWest corner of the house; 5 feet south of that corner". In one embodiment "Distance" in the above description is calculated as the cartesian distance in the abstract 2 dimensional space of RSSI and LQ: (measured RSSI–table RSSI)^2+(measured LQ–table LQ)^2. To one skilled in the art, there exists a number of ways of determining which of a set of possible values (physical location in this case) is best associated with a set of correlated measurements (RSSI and LQ in this case)—these algorithms are typically called Clustering algorithms.

Figure 8:
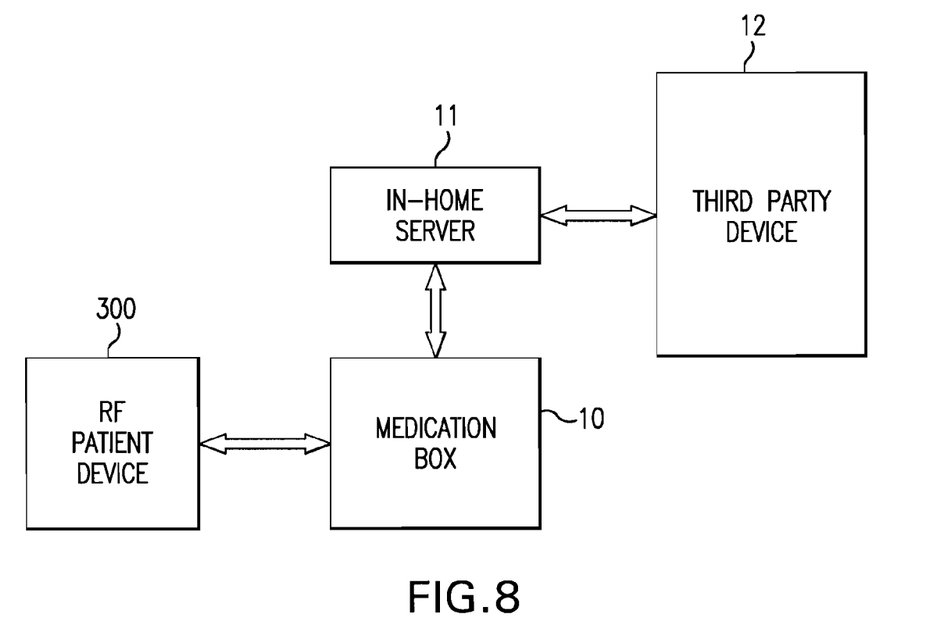
FIG. 8 shows an overall medication reminding system according to an embodiment of the invention.

FIG. 8 shows an overall medication reminding system according to an embodiment of the invention. As shown in FIG. 8, the medication box 10 is capable of communicating with the RF patient device 300. The patient device may be any device capable of wireless communication such as a PDA, wrist watch, cell phone, etc. The medication box 10 is also configured to communicate with an in-home server, such as a personal computer, which can store information and receive communication from a third party device 12 which is then passed on to the medication box 10. In this way, instructions from a patient's physician may be relayed to the patient via the medication box which is capable of communication, via the in-home server 11 or directly via a wireless connection, with a third party device 12. Information obtain by the medication box 10 may be stored at the medication box or transmitted to the in-home server 11 to be stored, and perhaps relayed to the third-party device 12 over known communication channels such as the Internet.

What is claimed is:

1. A medication box comprising:
   a processor configured to communicate with a transceiver;
   a plurality of compartments configured to store medication;
   the transceiver, wherein the transceiver is capable of communication with a patient via a RF user or patient device which is within communication range of the medication box; and
   a display that is configured to present at least one question or comment to a user or patient;
   wherein the medication box is configured to determine information about a location of the medication box relative to the RF user or patient device so as to prompt the patient or user to take a particular medication when the patient or user is within sufficiently close range of the medication box.

2. The medication box of claim 1, wherein the plurality of compartments have respective compartment doors configured to open and close the plurality of compartments.

3. The medication box of claim 2, wherein the plurality of compartment doors have respective switches capable of detecting whether the respective compartment door is open or closed.

4. The medication box of claim 3, wherein the switches are magnetic reed switches which are capable of detecting an open or closed state of the compartment door depending on whether the compartment door is opened a predetermine distance.

5. The medication box of claim 1, further comprising:
   an LCD;
   a speaker;
   a user input device; and
   a clock.

6. The medication box of claim 5, wherein the LCD is capable of providing information including at least a time of day, a date, and a pill to be taken at a particular time and capable of presenting at least one question to a user or patient.

7. The medication box of claim 5, wherein the user input device includes at least one input button which is configured to allow a user to manipulate the LCD and which is also configured to allow a user or patient to respond to respond to requests for information.

8. The medication box of claim 5, wherein the speaker is configured to present questions to a user or patient on a daily basis or at preset times.

9. The medication box of claim 8, wherein the user input device is configured to allow the
   user to answer the questions presented by the speaker and where the processor is configured to store data relating to the information input by the user input device.

10. The medication box of claim 1, further comprising a server which is configured to communicate information stored by the processor to a third-party device via wired or wireless communication methods.

11. The medication box of claim 10, wherein the server is configured to facilitate communication of information from the medication box over the Internet to a third-party device.

12. The medication box of claim 1, wherein the transceiver enables the medication box to be configured remotely.

13. The medication box of claim 1, wherein the transceiver is configured to measure signal strength and link communications quality of a radio signal which enables the medication box to determine information about a relative location of the medication box and the patient device that is an RF patient device which is capable of wirelessly communicating with the medication box.

14. The medication box of claim 1, wherein the medication box is capable of prompting a patient to take a particular medication if the transceiver determines that the patient is within sufficiently close range of the medication box.

15. The medication box of claim 3, wherein an estimated distance between the medication 1 box and the RF patient device can be determined by a received signal strength indicator measured by the medication box or by the W patient device.

16. A medication reminder system, comprising:
   a medication box having a processor configured to communicate with a transceiver, a plurality of compartments configured to store medication and the transceiver;
   an RF patient device capable of wireless communication with the medication box, wherein the medication box is configured to determine information about the location of the medication box relative to the RF patient device so as to prompt the patient or user to take a particular medication when the patient or user is within sufficiently close range of the medication box and to prompt a user or patient to take medication at a predetermined time.

17. The medication reminder system of claim 16, wherein the plurality of compartments have respective compartment doors configured to open and close the plurality of compartments.

18. The medication reminder system of claim 17, wherein the plurality of compartment doors have respective switches capable of detecting whether the respective compartment door is open or closed.

19. The medication reminder system of claim 18, wherein the switches are magnetic reed switches which are capable of detecting an open or closed state of the compartment door depending on whether the compartment door is opened a predetermine distance.

20. The medication reminder system of claim 16, wherein the medication box further comprises an LCD; a speaker; a user input device; and a clock.

21. The medication reminder system of claim 20, wherein the LCD is capable of providing information including at least a time of day, a date, and a pill to be taken at a particular time and capable of presenting at least one question to a user or patient.

22. The medication reminder system of claim 20, wherein the user input device includes at least one input button which is configured to allow a user or patient to manipulate the LCD and which is also configured to allow the user or the patient to respond to respond to requests for information.

23. The medication reminder system of claim 20, wherein the speaker is configured to present questions orally to a user or patient on a daily basis or at preset times.

24. The medication reminder system of claim 23, wherein the user input device is configured to allow the user or the patient to answer the questions presented by the speaker and where the processor is configured to store data relating to the information input by the user input device.

25. The medication reminder system of claim 16, further comprising a server which is configured to communicate information stored by the processor to a third-party device via wired or wireless communication methods.

26. The medication reminder system of claim 25, wherein the server the server is configured to facilitate communication of information from the medication box over the Internet to a third-party device.

27. The medication reminder system of claim 16, wherein the transceiver enables the medication box to be configured remotely.

28. The medication reminder system of claim 16, wherein the transceiver is configured to measure signal strength and link communications quality of a radio signal which enables the medication box to determine information about a relative location of the medication box and an RF patient device which is capable of wirelessly communicating with the medication box.

29. The medication reminder system of claim 16, wherein the medication box is capable of prompting a user or patient to take a particular medication if the transceiver determines that the patient is within sufficiently close range of the radio signal.

30. The medication reminder system of claim 16, wherein an estimated distance between the medication box and the RF patient device can be determined by a received signal strength indicator measured by the medication box or by the RF patient device.

* * * * *